United States Patent
Lei et al.

(10) Patent No.: US 9,427,141 B2
(45) Date of Patent: Aug. 30, 2016

(54) ENDOSCOPE-PIPE

(75) Inventors: Fang Lei, Durchhausen (DE); Ulrich Weiger, Rangendingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 599 days.

(21) Appl. No.: 12/817,723

(22) Filed: Jun. 17, 2010

(65) Prior Publication Data

US 2010/0324373 A1    Dec. 23, 2010

(30) Foreign Application Priority Data

Jun. 17, 2009    (DE) .................. 10 2009 025 659

(51) Int. Cl.
| | |
|---|---|
| *A61B 1/06* | (2006.01) |
| *A61B 1/07* | (2006.01) |
| *A61B 1/00* | (2006.01) |
| *G02B 23/24* | (2006.01) |

(52) U.S. Cl.
CPC ............ *A61B 1/07* (2013.01); *A61B 1/00096* (2013.01); *A61B 1/00167* (2013.01); *A61B 1/00179* (2013.01); *A61B 1/0607* (2013.01); *A61B 1/0623* (2013.01); *G02B 23/2423* (2013.01); *G02B 23/2469* (2013.01)

(58) Field of Classification Search
CPC   A61B 1/07; A61B 1/00096; A61B 1/00165; A61B 1/0607; A61B 1/0623
See application file for complete search history.

(56) References Cited

U.S. PATENT DOCUMENTS

| | | | | |
|---|---|---|---|---|
| 6,638,216 | B1 * | 10/2003 | Durell ......................... | 600/173 |
| 6,933,167 | B2 * | 8/2005 | Yamamoto .................. | 438/69 |
| 7,151,956 | B2 * | 12/2006 | Satoh ................... | A61B 5/0059 |
| | | | | 348/E5.029 |
| 2002/0107448 | A1 | 8/2002 | Gandjbakhche et al. | |
| 2003/0040657 | A1 * | 2/2003 | Yamaya et al. .............. | 600/107 |
| 2006/0052668 | A1 * | 3/2006 | Homma .................. | A61B 1/07 |
| | | | | 600/177 |
| 2007/0118013 | A1 * | 5/2007 | Miyagi et al. ................ | 600/129 |
| 2007/0270653 | A1 * | 11/2007 | Vayser et al. ................ | 600/182 |

FOREIGN PATENT DOCUMENTS

EP    2062545 A2    5/2009

\* cited by examiner

*Primary Examiner* — Anhtuan T Nguyen
*Assistant Examiner* — Alexandra Newton
(74) *Attorney, Agent, or Firm* — Whitmyer IP Group LLC

(57) ABSTRACT

An endoscope pipe with a central, elongated observation window on the distal end, whereby several light outlet openings for fiberoptic end surfaces are positioned close to the observation window for illuminating the angle area observed through the observation window and the light outlet openings are positioned asymmetrically in relation to the longitudinal extension of the observation window and/or the fiberoptic end surfaces are held in the light outlet openings in such a way that light is beamed from the fiberoptic end surfaces into the angle area in various directions.

16 Claims, 4 Drawing Sheets

ENDOSCOPE-PIPE

CROSS-REFERENCE TO RELATED APPLICATIONS

The present application claims priority of German patent application No. 10 2009 025 659.8 filed on Jun. 17, 2009.

FIELD OF THE INVENTION

The invention relates to an endoscope pipe. Endoscope pipes are parts of endoscopes that have applications especially in the field of minimally invasive surgery on humans or animals and, in rare cases, also in the field of technology.

BACKGROUND OF THE INVENTION

There are known endoscopes in the art that are configured in tubular form with pronounced length and are equipped on their distal end with an observation window, through which, in the case of an operation, it is possible to look into the surgical area situated in front of the distal end. Endoscopic instruments to perform surgical manipulation in the operating area can be inserted in the endoscope pipe through optional additional working channels. In addition, the end of the endoscope pipe comprises one or more light outlet openings, which are positioned around the round observation window and the openings of the working channels. It is common knowledge in the art to provide the light outlet openings for reception of fiberoptics, from whose end surfaces light emerges, so that a reliable illumination of the working areas is provided. The observation window is not necessarily required to be of circular configuration. These known endoscope pipes, in fact, typically demonstrate an unpleasantly non-homogeneous illumination of the working area, specifically in their use of non-circular illumination windows.

It is therefore the object of the invention to provide an endoscope pipe which ensures appropriate characteristics, so that the homogeneity of the illumination is improved, by taking into account the cross-section of the endoscope pipe and the shape of the distal end of the endoscope tube for the sake of a reliable and secure handling during surgical uses.

SUMMARY OF THE INVENTION

This object is achieved in one respect, through an endoscope pipe with a central, longitudinally extended observation window on the distal end and several light outlet openings, positioned close to the observation window, for fiberoptic end surfaces of fiberoptics for illuminating a solid angle area observed through the observation window, wherein the light outlet openings are positioned distributed along the longitudinal extension of the observation window and arranged asymmetrically to the longitudinal axis of the observation window. Advantageous elaborations of the inventive endoscope pipe are the subject of the subsidiary claims In another respect, the above mentioned objects are achieved through an endoscope pipe with a central, longitudinally extended observation window on the distal end and several light outlet openings, positioned close to the observation window, for fiberoptic end surfaces for illuminating the solid angle area observed through the observation window, wherein the fiberoptic end surfaces are held in the light outlet openings in such a way that light radiates out of the light outlet surfaces into the solid angle area in various directions.

A surprising discovery has been the fact that through an appropriate choice of arrangement or configuration of the light outlet openings around the elongated observation window, which is centrally positioned on the distal end of the endoscope pipe, it becomes possible to have a clearly improved and largely homogeneous illumination of the observed angle of vision, which need not necessarily contain the entire optical acquisition area.

In this regard it has proved especially effective to position the existing light outlet openings along the elongated shape of the observation window, so that the distribution shall occur asymmetrically to the longitudinal axis of the observation window. Thanks to this asymmetrical, i.e. non-uniform, arrangement of the light outlet openings, a very well-distributed homogenized distribution becomes possible. This is particularly the case when, along the length of the observation window, there has been an alternating arrangement of the light outlet windows, so that one on the right is followed by one on the left and so on, and in particular, in addition, the distances from the longitudinal center axis of the observation window or the distances along the length are varied or the areas of the light outlet openings are varied. The desired homogenization of the light distribution is successfully achieved thanks to this defined and deliberate non-homogenization of the arrangement of the light outlet openings that are situated only along the longitudinal extension of the observation window. A successful alternative has been to position and configure the fiberoptic end surfaces in the light outlet openings in such a way that the light descends from these in various directions into the working area or illumination area and in a predetermined solid angle area, so that this area is as homogeneously illuminated as possible. Surprisingly, the desired improved homogenization of the illumination is achieved as a result of these differentiations of the illumination directions, which include a non-homogenization of the illumination directions.

As a result of the inventive arrangement of the light outlet openings exclusively along the longitudinal extension of the observation windows, a relatively high number of outlet openings can successfully be selected and thereby a very good brightness can be achieved with good homogeneity in accordance with the invention. The inventive endoscope pipe thus proves itself well suited for difficult operations that require a highly reliable and good observation of the working area. The two aforementioned concepts have proved especially advantageous—first, the non-homogeneous distribution of the light outlet openings along the longitudinal extension of the observation windows and, second, the non-homogeneous selection of emission directions from the fiberoptic end surfaces of the light outlet openings. Through this combination, an especially efficient and homogeneous illumination of the relevant working area becomes possible. In addition, through this combination, the advantages of both concepts can be linked and moreover a decidedly closer arrangement of the light outlet openings becomes possible, along with either a reduction of the diameter of the endoscope pipe in case of predetermined light quantity for illuminating the relevant working areas, or conversely, in case of a predetermined diameter of the endoscope pipe, an increased light quantity. Either situation results in an increase in the possible application area of the inventive endoscope pipe compared with the endoscope pipe previously known in the art.

It has proved especially effective here to determine the emission direction for the light from the light outlet openings on the basis of having a prism or a holographic element positioned in the area of the fiberoptic end surfaces, by means of which the desired modification of the emission direction in relation to the light outlet opening from the fiberoptic end surface is determined. Owing to this arrangement of a prism or of a holographic element, it becomes possible, in a very defined and predetermined manner through the choice of prism or the configuration of the holographic element, to ensure a reliable and secure diversion of the light beam emerging from the fiberoptics into the desired direction for creating a distribution that is as homogeneous as possible. It has also proved effective here to use a prism or a holographic element for several neighboring fiberoptic end surfaces together. Consequently, on the one hand, it is possible to achieve a very compact structure and simple manufacturing along with secure, uniform deflection. The result is a very cost-effective realization of the inventive endoscope pipe. Alternatively or in addition, it has proved effective to configure the end surfaces of the fiberoptic or fiberoptics in such a way that the surface cuts the longitudinal axis of the fiberoptic at an angle not equal to 90 degrees. Through the choice of angle, a well-defined deflection of the emerging light becomes possible into the desired direction, varying according to the light outlet opening. It has proved especially advantageous here to combine several fiberoptics into one fiberoptic bundle and to cement them together in the light outlet opening and to configure the end surface of this bundle of fiberoptic ends and cement in such a way, in particular thou by grinding, that the surface becomes flat in part, and the desired angle of the fiberoptic end surfaces is achieved with respect to the longitudinal extension of the fiberoptics. This configuration ensures, on the one hand, that end surfaces very efficiently enable the transition from the optically thicker material to the environment in the desired emission direction and, on the other hand, that that there is a strongly insulated sealing of the light outlet opening and thereby of the interior space of the endoscope pipe. Thanks to this inventive insulating effect, sterilization in the manner of autoclaving finally becomes a realistic possibility.

It has proved especially advantageous to position the prism or prisms, or the holographic element or elements, between the fiberoptic end surfaces and the light outlet openings, and to cement these as a unit together with the fiberoptics. It has proved effective here to use an optically inactive cement that has an index of refraction corresponding to that of the fiberoptics or of the prism or of the holographic element.

The observation window is advantageously in the form of a curved observation window, in particular with a cylindrical dome, because the shaft is curved in the direction of the longitudinal extension of the shaft. This configuration makes it possible to increase the length of the observation window and thereby the area for positioning the light outlet openings and consequently to ensure a more extensive homogeneous illumination of the working area in the area in front of and to the sides of the distal end of the endoscope. As a result of the curved configuration of the endoscope window, the observation range of the endoscope is also considerably enlarged through the corresponding configuration of the lens below the observation window. The result is a very effective and useful endoscope pipe.

Container sleeves are preferably provided in the light outlet surfaces, to direct the fiberoptics and fiberoptic end surfaces which in turn allows an adjustment of the desired emission direction of the light from the light outlet openings in simple, reliable manner.

The present invention is described in greater detail hereafter with reference to the illustrations of one selected example of the invention. The invention is not restricted to this illustrative example.

DETAILED DESCRIPTION OF THE INVENTION

Figure 1:
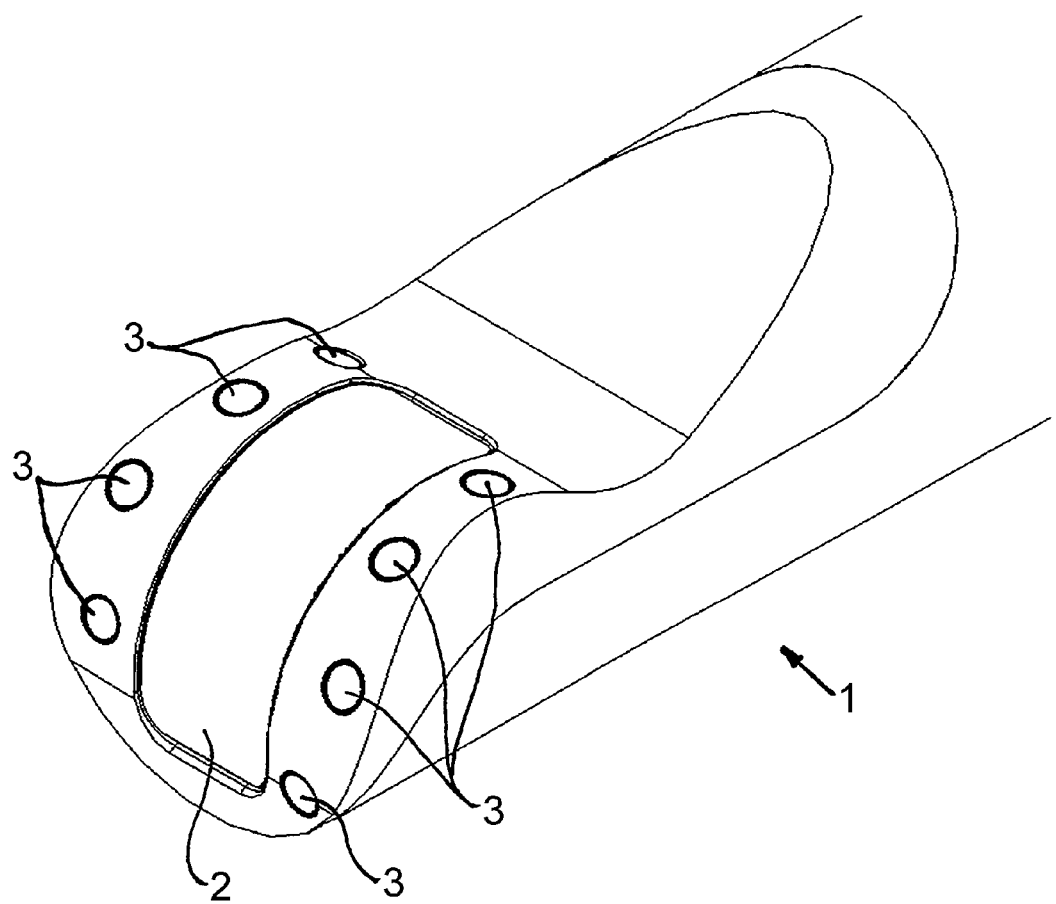
FIG. 1 shows a side view of the distal end of the inventive endoscope pipe.

FIG. 1 shows in a diagonal view the distal end 1 of the inventive endoscope pipe. Shown at the center is the observation window 2, which is longitudinally extended in configuration and is positioned at the center in the area of the distal end 1. The observation window 2 here is configured as continuously curved, so that the curve extends similarly to a cylinder in the longitudinal direction of the endoscope pipe. The observation window here shows an essentially rectilinear shape, which is configured as essentially cylindrically curved.

The light outlet openings 3 are positioned along the longitudinal extension of the observation window 2. There are a total of eight light outlet openings, which are positioned opposite one another and asymmetrically to the longitudinal extension of the longitudinal axis of the observation window. They are placed at varying distances from the longitudinal axis or are offset in alternation along the longitudinal axis of the observation window 2. These eight light outlet surfaces are of similar configuration. Positioned in these light outlet surfaces are a bundle of fiberoptic end surfaces, which are cemented together so that the light outlet surfaces are configured as insulated against gas and fluids and thus are autoclavable.

Because of the asymmetrical arrangement of the light outlet openings 3 along the observation window 2, it becomes possible, first, to emit the light from the fiberoptic end surfaces in various spatial directions, in particular because of the aforementioned dome of the end area with the observation window 2 of the distal end 1 of the inventive endoscope pipe, and, second, because of this offset arrangement, the non-homogeneous arrangement of the light outlet openings, to create a homogenized illumination of the working and observation area for a micro-invasive intervention.

Figure 2:
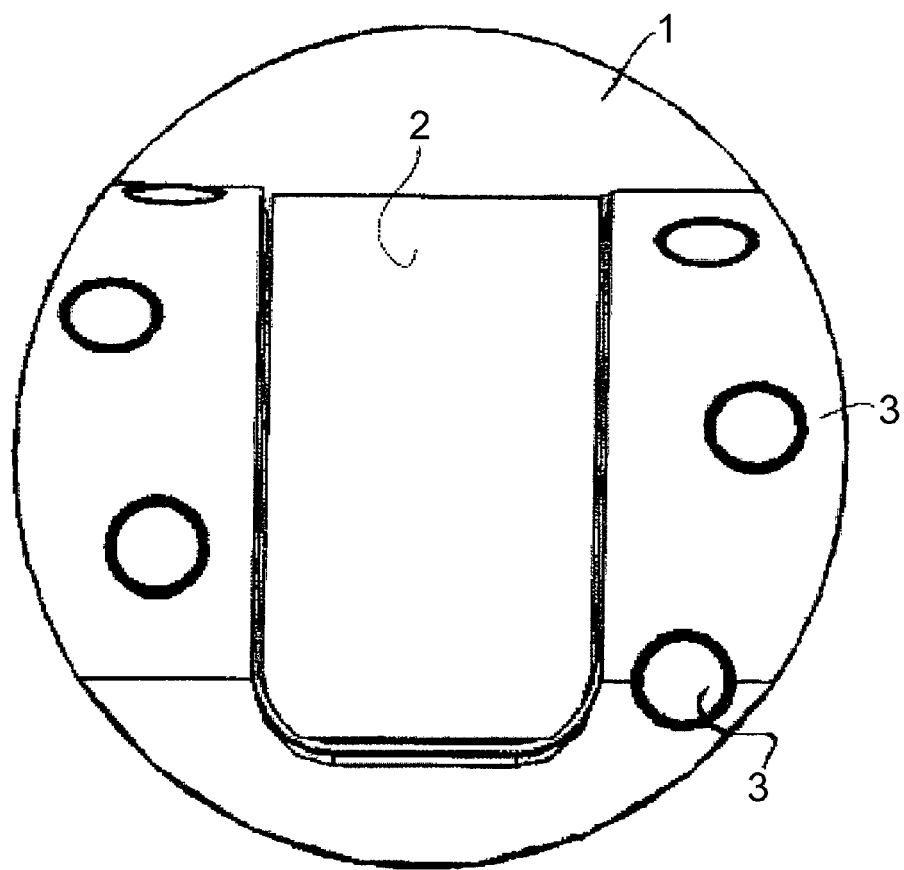
FIG. 2 shows a front view of the distal end of the inventive endoscope pipe.

FIG. 2 presents a view from the front toward the circular endoscope pipe with the distal end 1 and the observation window 2 as described. Laterally, at varying distances, various light outlet openings 3 are positioned along the longitudinal extension of the observation window 2. As a result of the non-homogeneous arrangement of the observation window 2, the desired homogenization of the illumination of the working area is achieved.

Figure 3:
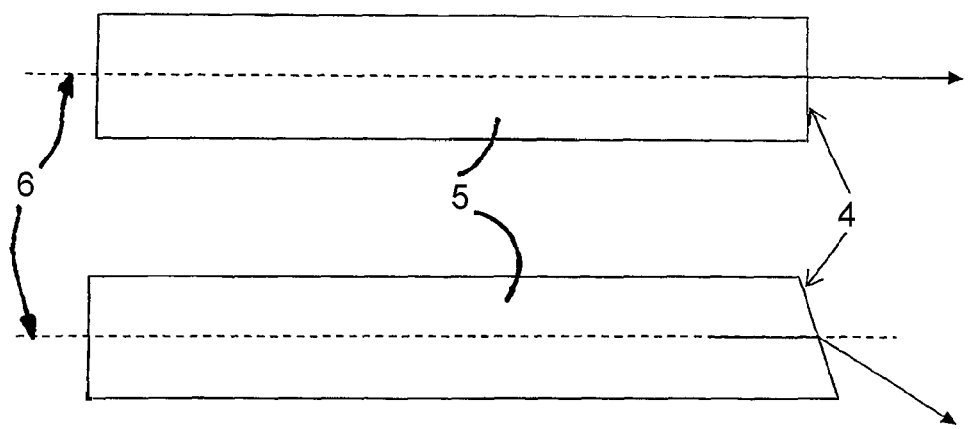
FIG. 3 schematically shows the configuration of individual fiberoptics and individually configured fiberoptic end surfaces.

FIG. 3 shows two examples of fiberoptics 5. The fiberoptics 5 end in fiberoptic end surfaces 4. The fiberoptic end surfaces 4 constitute level surfaces that are at a defined angle to the longitudinal extension of the fiberoptic 5. It has proved especially preferential to configure individual fiberoptic end surfaces 4, or all fiberoptic end surfaces 4, at an angle not equal to 90 degrees and thereby to ensure an illumination by the emitted lights that is diagonal or at a predetermined angle from the longitudinal extension 6 of the fiberoptic 5. Through the choice of angle, very carefully differentiated illumination scenarios can be created to achieve the most homogeneous possible illumination of the working area. In certain embodiments, the light is broken at the fiberoptic end surfaces, so that the fiberoptic end surfaces form an angle not equal to 90 degrees to a longitudinal axis of the fiberoptics. "Light is broken" is defined to mean "refracted."

Figure 4:
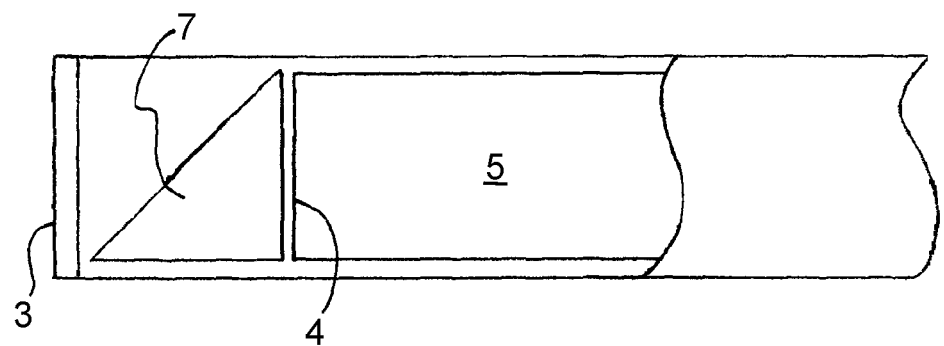
FIGS. 4-6 show examples of components inside of the light outlet openings.
Figure 5:
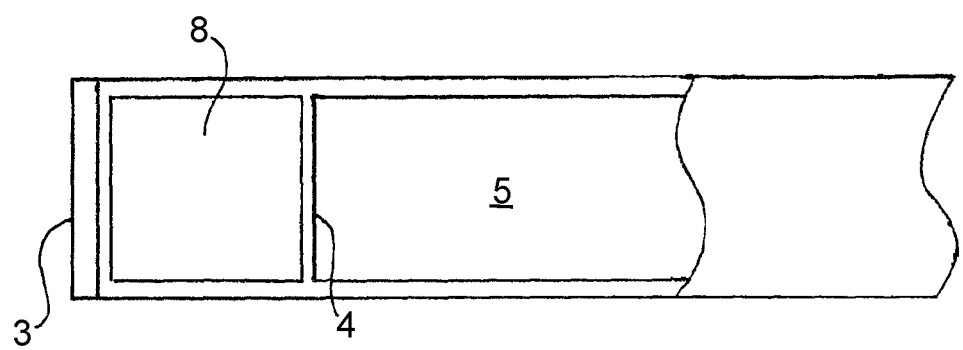
Figure 6:
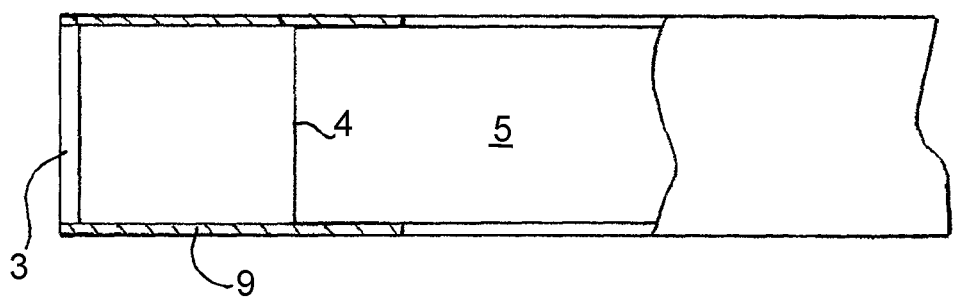

FIG. 4 shows an example of the inside of the light outlet openings 3. In FIG. 4, a prism 7 is shown between the fiberoptic end surfaces 4 and the light outlet openings 3. FIG. 5, a holographic element 8 is shown between the fiberoptic end surfaces 4 and the light outlet openings 3. In FIG. 6, a sleeve 9 is shown between the fiberoptic end surfaces 4 and the light outlet openings 3. In certain embodiments, the prism 7, holographic element 8 and sleeve 9 are cemented together as a unit with the fiberoptics 5.

What is claimed is:

1. An endoscope pipe having a distal end, the endoscope pipe comprising:
   an observation window on the distal end of the endoscopic pipe, the observation window extending along a longitudinal window axis between a first end and an opposing second end, the observation window having a first side and an opposing second side each extending between the first and second ends of the observation window, the observation window having a continuously curved shape along the window axis;
   first and second light outlet openings for transmitting light therethrough, the first and second light outlet openings distributed along the first side of the observation window such that a distance extending between the first light outlet opening and the first side of the observation window in a direction perpendicular to the window axis is greater than a distance extending between the second light outlet opening and the first side of the observation window in a direction perpendicular to the window axis; and
   fiberoptic end surfaces of fiberoptics positioned in the first and second light outlet openings for illuminating an angle area observed through the observation window.

2. The endoscope pipe of claim 1, wherein the fiberoptic end surfaces are held in the first and second light outlet openings in such a way that light radiates out of the light outlet surfaces into the solid angle area in at least two spatial directions.

3. The endoscope pipe of claim 1, wherein at least one prism is provided in the area of the fiberoptic end surfaces.

4. The endoscope pipe of claim 3, wherein the prism is positioned between the fiberoptic end surfaces and the first and second light outlet openings.

5. The endoscope pipe of claim 1, wherein a holographic element is provided in the area of the fiberoptic end surfaces to emit beams in at least two spatial directions.

6. The endoscope pipe of claim 5, wherein the holographic element is positioned between the fiberoptic end surfaces and the first and second light outlet openings.

7. The endoscope pipe of claim 1, wherein the distal end of the endoscope pipe is curved in the direction of the first side of the observation window, and in particular is cylindrically curved.

8. The endoscope pipe of claim 1, wherein container sleeves are inserted in the first and second light outlet openings for directing the fiberoptic end surfaces.

9. The endoscope pipe of claim 1, wherein the first and second light outlet openings are arranged in a non-homogenized manner.

10. The endoscope of claim 1, wherein a distance extends between the first and second light outlet openings in a direction parallel to the window axis.

11. The endoscope of claim 1, further comprising:
    third and fourth light outlet openings disposed relative to the distal end portion of the endoscope and proximate the second side of the observation window, the third and fourth light outlet openings positioned relative to the observation window such that a distance extending between the third light outlet opening and the second side of the observation window in a direction perpendicular to the window axis is greater than a distance extending between the fourth light outlet opening and the second side of the observation window in a direction perpendicular to the window axis.

12. The endoscope of claim 11, wherein a distance extends between the third and fourth light outlet openings in a direction parallel to the window axis.

13. The endoscope of claim 11, wherein (i) the first and second light outlet openings and (ii) the third and fourth light outlet openings are asymmetrically aligned relative to the window axis.

14. An endoscope pipe having a distal end, the endoscope pipe comprising:
    an observation window on the distal end of the endoscopic pipe, the observation window extending along a longitudinal window axis between a first end and an opposing second end, the observation window having a first side and an opposing second side each extending between the first and second ends of the observation window, the observation window having a continuously curved shape along the window axis;
    first and second light outlet openings for transmitting light therethrough, positioned close to the first side of the observation window such that a distance extending between the first light outlet opening and the first side of the observation window in a direction perpendicular to the window axis is greater than a distance extending between the second light outlet opening and the first side of the observation window in a direction perpendicular to the window axis; and
    fiberoptic end surfaces for illuminating an angle area observed through the observation window,
    wherein the fiberoptic end surfaces are held in the first and second light outlet openings in such a way that light radiates out of the light outlet surfaces into the angle area in at least two spatial directions.

15. A process of manufacturing an endoscope pipe, the process comprising:
    providing an observation window on a distal end of an endoscopic pipe, the observation window extending along a longitudinal window axis between a first end and an opposing second end, the observation window having a first side and an opposing second side each extending between the first and second ends of the observation window, the observation window having a continuously curved shape along the window axis;
    positioning first and second light outlet openings for transmitting light therethrough in the distal end of the endoscopic pipe, the first and second light outlet openings distributed along the first side of the observation window such that a distance extending between the first light outlet opening and the first side of the observation window in a direction perpendicular to the window axis is greater than a distance extending between the second light outlet opening and the first side of the observation window in a direction perpendicular to the window axis; and positioning fiberoptic end surfaces of fiberoptics in each of the first and second light outlet openings for illuminating a solid angle area observed through the observation window, wherein in each of the first and second light outlet openings, the ends of the fiberoptics are combined into one fiberoptic bundle and are connected with a cement to cement the ends together in each of the first and second light outlet openings.

16. The process of claim 15, wherein grinding is used to allow the common end surface to become flat in part, and the desired angle of the fiberoptic end surfaces is achieved with respect to the longitudinal extension of the fiberoptic.

* * * * *